United States Patent
Majeed et al.

(10) Patent No.: US 9,050,284 B2
(45) Date of Patent: Jun. 9, 2015

(54) ORALLY BIOAVAILABLE STILBENOIDS—COMPOSITIONS AND THERAPEUTIC APPLICATIONS THEREOF

(75) Inventors: Muhammed Majeed, Piscataway, NJ (US); Jeffrey Reinhardt, Carson City, NV (US); Kalyanam Nagabhushanam, Piscataway, NJ (US); Samuel Manoharan Thomas, Bangalore (IN); Krishnamani Jayaraman, Bangalore (IN)

(73) Assignee: Sami Labs Limited, Bangalore (IN)

( * ) Notice: Subject to any disclaimer, the term of this patent is extended or adjusted under 35 U.S.C. 154(b) by 846 days.

(21) Appl. No.: 12/367,840

(22) Filed: Feb. 9, 2009

(65) Prior Publication Data

US 2010/0204339 A1    Aug. 12, 2010

(51) Int. Cl.
| | |
|---|---|
| A61K 31/05 | (2006.01) |
| A61K 31/075 | (2006.01) |
| A61K 31/09 | (2006.01) |
| C07C 39/20 | (2006.01) |
| C07C 39/21 | (2006.01) |
| C07C 43/23 | (2006.01) |
| A01N 31/14 | (2006.01) |

(52) U.S. Cl.
CPC ............ *A61K 31/09* (2013.01); *A01N 31/14* (2013.01); *C07C 39/20* (2013.01); *A61K 31/05* (2013.01); *A61K 31/075* (2013.01); *C07C 39/21* (2013.01); *C07C 43/23* (2013.01)

(58) Field of Classification Search
CPC ..... A61K 31/05; A61K 31/075; A61K 31/09; C07C 39/20; C07C 39/21; C07C 43/23
USPC .................. 514/476; 568/717, 744
See application file for complete search history.

(56) References Cited

U.S. PATENT DOCUMENTS

2003/0171429 A1 * 9/2003 Chen et al. ............... 514/475
2007/0116779 A1 * 5/2007 Mazzio .................... 424/539

FOREIGN PATENT DOCUMENTS

CN   101070273   * 11/2007
WO   WO 2005065667 A2 * 7/2005

OTHER PUBLICATIONS

Ohguchi et. al., Bioscience, Biotechnology, and Biochemistry, 2003, Japan Society for Bioscience, Biotechnology and Agrochemistry, vol. 67, No. 3, pp. 663-665.*
Ma et. al., Fitoterapia, 2002, Elsevier, vol. 73, pp. 313-315.*

* cited by examiner

Primary Examiner — Sarah Pihonak

(57) ABSTRACT

Disclosed is a novel sirtuin modulating composition comprising an orally bioavailable SIRT-1 enhancing compound 3,5-dimethoxy-3',4'-dihydroxystilbene represented by STR#I. Also disclosed is an anti-acne composition comprising 3,5-dimethoxy-3',4'-dihydroxystilbenes represented by STR#I. Further, a novel sirtuin modulating composition comprising an orally bioavailable SIRT-1 enhancing compound 2,3',5',6-tetrahydroxy-trans-stilbene represented by STR#II is also disclosed.

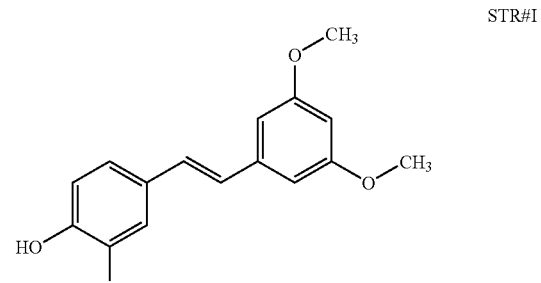

STR#I

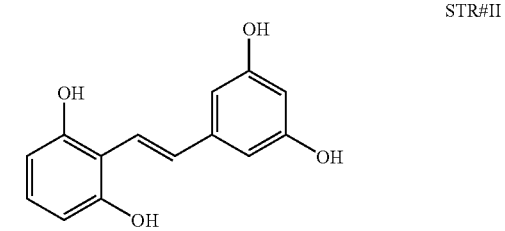

STR#II

2 Claims, 10 Drawing Sheets

ORALLY BIOAVAILABLE STILBENOIDS—COMPOSITIONS AND THERAPEUTIC APPLICATIONS THEREOF

BACKGROUND OF THE INVENTION

1. Field of the Invention

The present invention in general relates to natural stilbenoids. More specifically, the present invention relates to situin modulating stilbenoids, in specific orally bioavailable SIRT-1 enhancing compounds (i) 3,5-dimethoxy-3,4'-dihydroxystilbene and (ii) 2,3',5',6-tetrahydroxy-trans-stilbene, and compositions thereof. The present invention also discusses the novel enhanced anti-acne properties of 3,5-dimethoxy-3,4'-dihydroxystilbene and compositions thereof.

2. Description of Prior Art

SIRT1 is a member of the sirtuin family of $NAD^+$-dependent deacetylases. SIRT1 is an enzyme which deacetylates proteins that contribute to cellular regulation (reaction to stressors, longevity). These enzymes have evolved to catalyze a unique reaction in which deacetylation of a lysine residue in a substrate protein is coupled to the consumption of NAD. The following prior art references discuss the biological nature and activity of SIRT1.

I. Frye, R. A. Characterization of five human cDNAs with homology to the yeast SIR2 gene: Sir2-like proteins (sirtuins) metabolize NAD and may have protein ADP-ribosyltransferase activity. Biochem Biophys Res Commun 260, 273-9 (1999); II. Frye, R. A. Phylogenetic classification of prokaryotic and eukaryotic Sir2-like proteins. Biochem Biophys Res Commun 273, 793-8 (2000); III. Imai, S., Armstrong, C. M., Kaeberlein, M. & Guarente, L. Transcriptional silencing and longevity protein Sir2 is an NAD-dependent histone deacetylase. Nature 403, 795-800 (2000)].

The modulation of the activities of cellular protein substrates including PGC-1α, NCoR, p300, NFkB, FOXO, and p53 has been attributed to the biological effects of the enzyme on mitochondrial biogenesis, metabolism in muscle and adipose tissue, and cellular survival. Activation of SIRT1 protein results in improvement of insulin sensitivity, lower glucose levels; Thus SIRT1 inhibition has direct bearing on diabetic control, SIRT1 activation results in the increase in the number of mitochondria and improvement of their function. Increase in mitochondrial number has direct attributes to longevity of the cell. SIRT1 activation is related to decreased adipocity and tolerance to exercise. Thus SIRT1 activation has application in weight control and control of obesity. References include:

1. Bouras, T. et al. SIRT1 deacetylation and repression of p300 involves lysine residues 1020/1024 within the cell cycle regulatory domain 1. J Biol Chem 280, 10264-76 (2005);
2. Brunet, A. et al. Stress-dependent regulation of FOXO transcription factors by the SIRT1 deacetylase. Science 303, 2011-5 (2004);
3. Luo, 3. et al. Negative control of p53 by Sir2alpha promotes cell survival under stress. Cell 107, 137-48 (2001);
4. Motta, M. C. et al. Mammalian SIRT1 represses fork head transcription factors. Cell 116, 551-63 (2004);
5. Nemoto, S., Fergusson, M. M. & Finkel, T. SIRT1 functionally interacts with the metabolic regulator and transcriptional co-activator PGC-1 {alpha}. J Biol Chem 280, 16456-60 (2005);
6. Picard, F. et al. Sirt1 promotes fat mobilization in white adipocytes by repressing PPAR-gamma. Nature 429, 771-6 (2004);
7. Rodgers, 3. T. et al. Nutrient control of glucose homeostasis through a complex of PGC-1alpha and SIRT1. Nature 434, 113-8 (2005);
8. Van der Horst, A. et al. FOXO4 is acetylated upon peroxide stress and deacetylated by the longevity protein hSir2(SIRT1). I Biol Chem 279, 28873-9 (2004);
9. Vaziri, H. et al. hSIR2 (SIRT1) functions as an NAD-dependent p53 deacetylase. Cell 107, 149-59 (2001);
10. Yeung, F. et al. Modulation of NF-kappaB-dependent transcription and cell survival by the SIRT1 deacetylase. Embo 3 23, 2369-80 (2004).
11. Elliot, P. J.; lirousek, J.; Sirtuins, Novel targets for metabolic diseases, Current Opinion in Investigational drugs, 9(4), 371-8 (2008)

The ability of resveratrol to modulate sirtuin gene and protein expression has been well documented. Some important prior art in this regard include:

I. The protective action of resveratrol in upregulating the SIRT1-AMPK (AMP-activated kinase) signaling system in preventing alcohol induced fatty liver in ethanol-fed mice is documented in Am J Physiol Gastrointest Liver Physiol. 2008 October; 295(4):G833-42.

II. Pharmacological preconditioning by resveratrol in part is directed towards the compound's ability to activate SIRT1 in 1: Med Hypotheses. Aug. 9, 2008.

III. The ability of resveratrol to elevate glucose uptake in muscle cells through a mechanism involving sirtuins and AMP-kinase and possibly stimulation of GLUT4 transporter intrinsic activity has been implicated in Biochem Biophys Res Commun. Sep. 12, 2008; 374(1):117-22.

Similarly, the ability of resveratrol to inhibit *Propionibacterium acnes* has been documented in 3 Antimicrob Chemother. 2007 June; 59(6):1182-4.

The principle objective of the present invention is to evaluate the bioavailability and sirtuin modulating ability of 3,5-dimethoxy-3,4'-dihydroxystilbene which are analogs of 3,5-dimethoxy-4'-hydroxystilbene (pterostilbene) which in turn are natural analogs of resveratrol. The invention also aims to evaluate the bioavailability and sirtuin modulating ability of 2,3',5',6-tetrahydroxy-trans-stilbene (gnetol).

It is also another objective of the present invention to evaluate 3,5-dimethoxy-3,4'-dihydroxystilbene (3-hydroxypterostilbene) for its potential to inhibit *Propionibacterium acnes* and cosmeceutical applications thereof.

The present invention fulfills the aforesaid objectives and provides further related advantages.

SUMMARY OF THE INVENTION

The present invention discloses a novel composition comprising an orally bioavailable sirtuin modulating compound 3,5-dimethoxy-3,4'-dihydroxystilbene, said composition enhancing the SIRT1 polypeptide activity more effectively than resveratrol (3,4',5-trihydroxy-trans-stilbene) or its natural methoxylated derivative 3,5-dimethoxy-4'-hydroxystilbene (pterostilbene). The invention also discloses a novel composition comprising an orally bioavailable sirtuin modulating compound comprising 2,3',5',6-tetrahydroxy-trans-stilbene (gnetol), said composition enhancing the SIRT1 polypeptide activity more effectively than resveratrol (3,4',5-trihydroxy-trans-stilbene), its natural methoxylated derivative 3,5-dimethoxy-4'-hydroxystilbene (pterostilbene) or pterostilbene analog namely 3,5-dimethoxy-3,4'-dihydroxystilbene. In addition, the invention also discloses an anti-acne composition comprising pterostilbene analog 3,5-dimethoxy-3,4'-dihydroxystilbene, said analog inhibiting the growth of *Propionibacterium acnes* more effectively than resveratrol (3,4',5-trihydroxy-trans-stilbene). The advantages of the present invention may be summarized as follows.
1. A novel sirtuin modulating composition comprising orally bioavailable 3,5-dimethoxy-3,4'-dihydroxystilbene, said composition enhancing the SIRT1 polypeptide activity more effectively than resveratrol (3,4',5-trihydroxy-trans-stilbene) or its natural methoxylated derivative 3,5-dimethoxy-4'-hydroxystilbene (pterostilbene).
2. A novel sirtuin modulating composition comprising orally bioavailable 2,3',5',6-tetrahydroxy-trans-stilbene (gnetol) enhancing the SIRT1 polypeptide activity more effectively than resveratrol (3,4',5-trihydroxy-trans-stilbene), its natural methoxylated derivative 3,5-dimethoxy-4'-hydroxystilbene (pterostilbene) or pterostilbene analog namely 3,5-dimethoxy-3,4'-dihydroxystilbene.
3. An anti-acne composition comprising pterostilbene analog 3,5-dimethoxy-3,4'-dihydroxystilbene, said analog inhibiting the growth of *Propionibacterium acnes* more effectively than resveratrol (3,4',5-trihydroxy-trans-stilbene).

Other features and advantages of the present invention will become apparent from the following more detailed description, taken in conjunction with the accompanying drawings, which illustrate, by way of example, the principle of the invention.

Figure 1A:
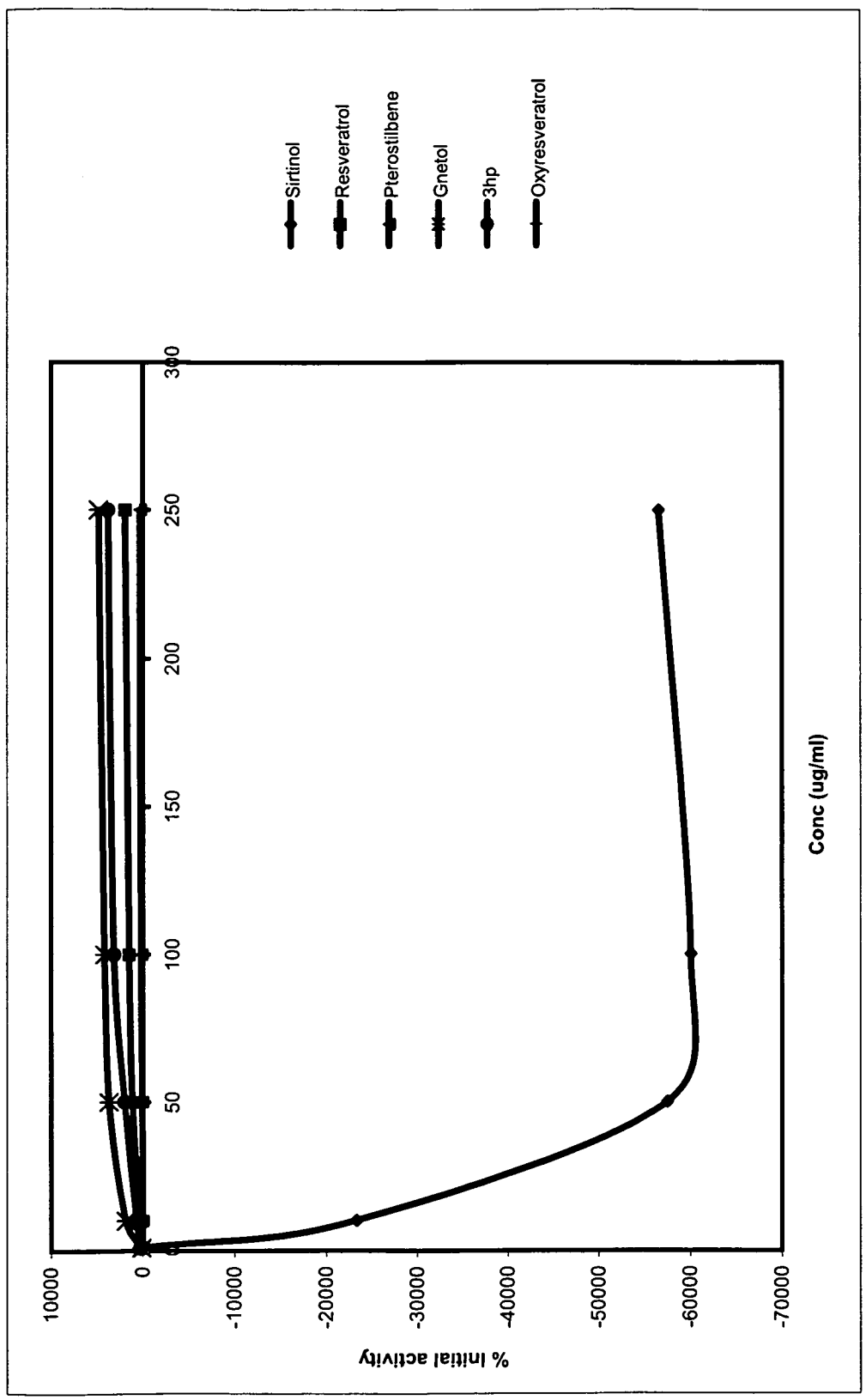
FIGS. 1A and 1B represents a graphical representation of the comparative percentage initial activity of the SIRT1 polypeptide activity with increasing concentrations of Sirtinol, Resveratrol, Pterostilbene, Gnetol, 3-hydroxypterostilbene (3 hp) and oxyresveratrol.

DETAILED DESCRIPTION OF THE MOST PREFERRED EMBODIMENT (FIGS. 1, 2, 3, 4 and 5)

In the most preferred embodiment, the present invention relates to a novel sirtuin modulating composition comprising orally bioavailable 3,5-dimethoxy-3,4'-dihydroxystilbene represented by STR#1, said composition enhancing the SIRT1 polypeptide activity more effectively than resveratrol (3,4',5-trihydroxy-trans-stilbene) or its natural methoxylated derivative 3,5-dimethoxy-4'-hydroxystilbene (pterostilbene).

In another preferred embodiment, the present invention relates to a novel sirtuin modulating composition comprising bioavailable 2,3',5',6-tetrahydroxy-trans-stilbene (gnetol) represented by STR#2, said composition enhancing the SIRT-I gene and polypeptide activity more effectively than resveratrol (3,4',5-trihydroxy-trans-stilbene), its natural methoxylated derivative 3,5-dimethoxy-4'-hydroxystilbene (pterostilbene) or pterostilbene analog 3,5-dimethoxy-3,4'-dihydroxystilbene (3-hydroxypterostilbene).

In an additional embodiment, the present invention also relates to an anti-acne composition comprising pterostilbene analog 3,5-dimethoxy-3,4'-dihydroxystilbene represented by STR#1, said analog inhibiting the growth of *Propionibacterium acnes* more effectively than resveratrol (3,4',5-trihydroxy-trans-stilbene).

In an alternate embodiment, the present invention relates to a sirtuin modulating stilbenoid 3,5-dimethoxy-3,4'-dihydroxystilbene represented by STR#1, said stilbenoid in particular capable of enhancing SIRT-1 polypeptide activity. In one specific embodiment, said stilbenoid occurs in a cosmeceutical formulation. In another specific embodiment, said stilbenoid occurs in a nutraceutical formulation. In a more specific embodiment, said stilbenoid occurs in a pharmaceutical formulation.

In yet another alternate embodiment, the present invention relates to a sirtuin modulating stilbenoid 2,3',5',6-tetrahydroxy-trans-stilbene (gnetol) represented by STR#2, said stilbenoid in particular capable of enhancing SIRT-1 polypeptide activity. In one specific embodiment, said stilbenoid occurs in a cosmeceutical formulation. In another specific embodiment, said stilbenoid occurs in a nutraceutical formulation. In a more specific embodiment, said stilbenoid occurs in a pharmaceutical formulation.

In yet another alternate embodiment, the present invention also relates to anti-acne stilbenoid 3,5-dimethoxy-3,4'-dihydroxystilbene, said stilbenoid in particular capable of inhibiting the growth of *Propionibacterium acnes*. In one specific embodiment, said stilbenoid occurs in a cosmeceutical formulation. In another specific embodiment, said stilbenoid occurs in a pharmaceutical formulation.

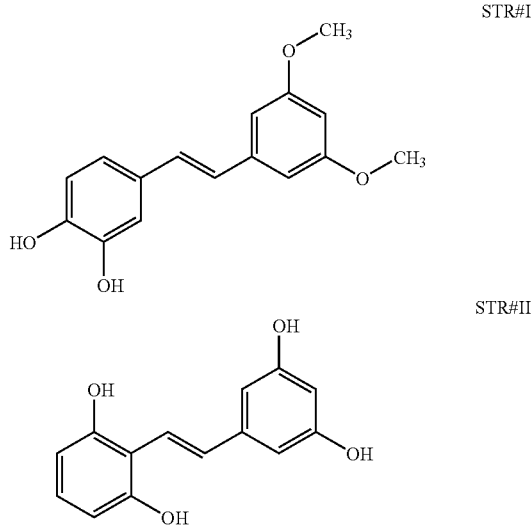

The underlying paragraphs discuss in detail the sirtuin modulating properties of 3,5-dimethoxy-3,4'-dihydroxystilbene and 2,3',5',6-tetrahydroxy-trans-stilbene (gnetol) in comparison (EXAMPLE I, FIGS. 1A and 1B AND Table A) to resveratrol (3,4',5-trihydroxy-trans-stilbene), its natural methoxylated derivative 3,5-dimethoxy-4'-hydroxystilbene (pterostilbene) and Oxyresveratrol (trans-2,3',4,5'-tetrahydroxystilbene).

EXAMPLE I

Figure 1B:
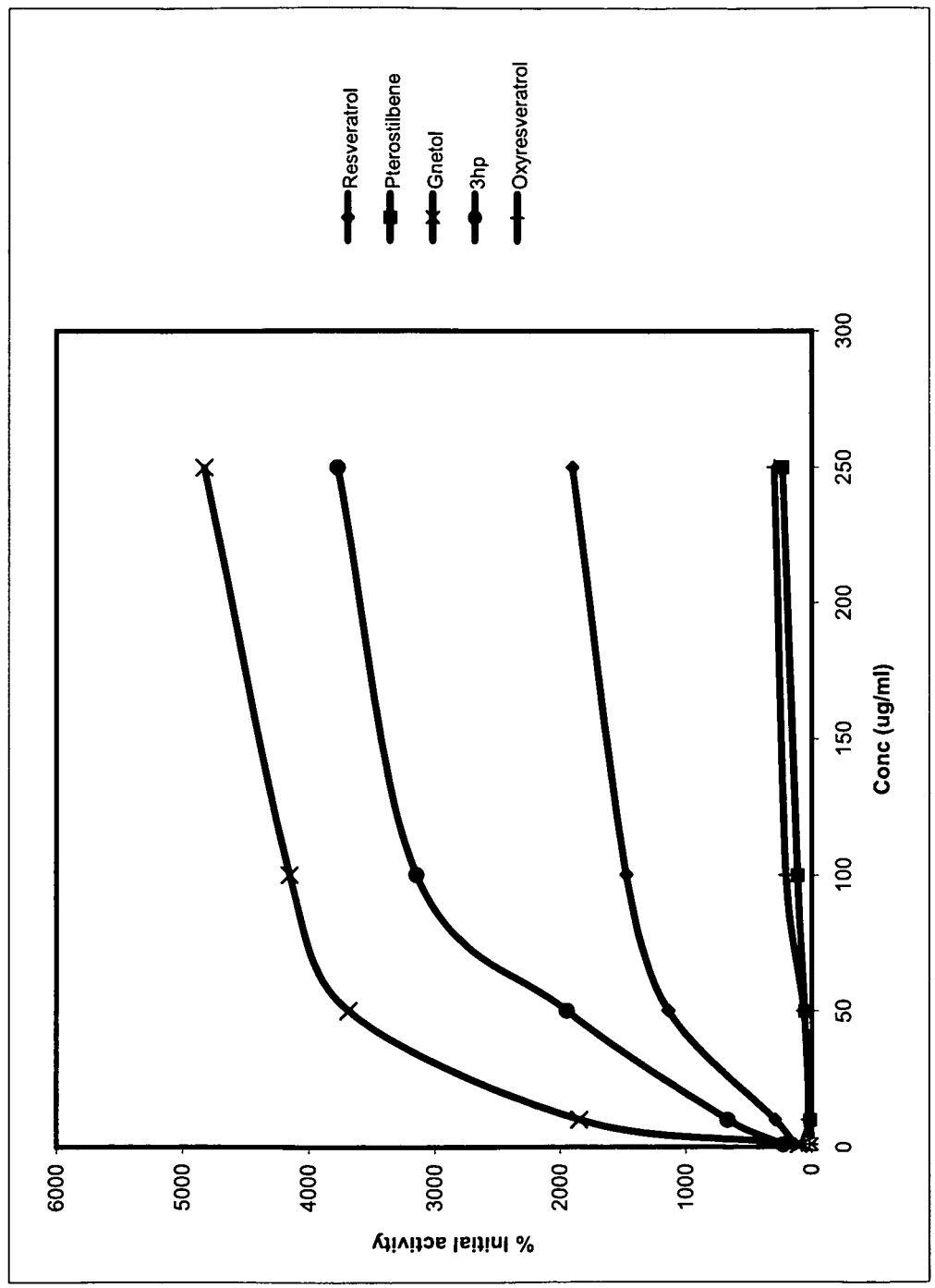

FIGS. 1A and 1B

SIRT-1 activation/inhibition was measured using the SIRT1 Direct fluorescent Screening Assay kit (Catalog No.

10010401) and instructions provided therein of Cayman Chemical Company, 1180 East Ellsworth Road, Ann Arbor, Mich. 48108 USA.

Table A

Results (Table A) and Discussion

It may be known from Table A that both 3,5-dimethoxy-3,4'-dihydroxystilbene (3-hydroxypterostilbene) and 2, 3',5',6-tetrahydroxy-trans-stilbene (gnetol) show enhanced percentage SIRT 1 modulation in comparison to resveratrol, Pterostilbene and Oxyresveratrol at concentrations ranging from 10 μg/ml to 250 μg/ml. 2,3',5',6-tetrahydroxy-trans-stilbene (gnetol) proves to be a better SIRT1 activator at concentrations ranging from 10 μg/ml to 250 μg/ml than 3-hydroxypterostilbene. Since SIRT-1 enhancing properties of a molecule confer on them the ability to control glucose levels; increase the longevity of cells by increasing the number and efficient-functioning of mitochondrial components; control obesity, compositions containing such compounds are useful in control of diabetic conditions and obesity. Added advantage is the oral bioavailability of these two compounds, namely 3,5-dimethoxy-3,4'-dihydroxystilbene (3-hydroxypterostilbene 3 hp)) and 2,3',5',6-tetrahydroxy-trans-stilbene (gnetol) as demonstrated by our data in FIG. 2A, FIG. 2B, FIG. 3A, FIG. 3B, FIG. 3C, FIG. 4, FIG. 5A & FIG. 5B.

10. Sterile disc 6 mm.
11. Samples tested: Resveratrol (Batch No.: C81173) and 3-Hydroxypsterostilbene (Batch No.: P80096)

Methods

Anaerobic Chamber

The chamber used in the study is of COY LABORATORY USA model 8301-230, 3 ft polymer. The anaerobic chamber consists of a main chamber where in all the operations and incubation of the culture are carried out and a transfer chamber which is meant for taking the materials in and out of the equipment. The main chamber is provided with a heated fan box in order to maintain the required temperature (37° C.) and to circulate the air in the chamber. A catalyst stakpak is fixed to this fan box which consists of palladium catalyst, which is meant to convert oxygen to water molecules by reacting with hydrogen molecules. The anaerobic condition in the chamber for this is maintained by initialization with Nitrogen gas and then by the Mixture gas of $N_2+H_2+CO_2$ in the proportion 80:10:10. Two gas tank arrangements have been done where only $N_2$ is connected to the transfer chamber.

Preparation of the Inoculum

*Propionibacterium acnes* ATCC: 11827

To carry out the antimicrobial activity of the products against *P. acnes* the organism was first cultured in the anaerobic conditions. Culture was inoculated into pre-sterile reinforced *Clostridium* medium (RCM) and incubated at anaerobic condition for 24 hrs. 24 hr to 48 hrs culture at Optical Density @625 nm was determined 0.632 (1:2 dilution) 4.0 Macfarland standards.

Procedure 30 ml of sterilized RCM was poured into the pre-sterile Petri plates inside the chamber and allowed to solidify. The culture was inoculated (0.2 ml/plate) and spread evenly. After 30 minutes, antibacterial sterile discs (6 mm) were dispensed. Samples in varying concentrations (0.4-5% w/v) were prepared using dimethylsulphoxide (DMSO) as the solvent. 10 μl of the prepared sample and controls were dispensed onto the discs. The plates were incubated inside the anaerobic chamber at 37° C. for 24 to 48 hours duration.

Results and Discussion (Table B)

TABLE A

Percentage SIRT 1 modulation by stilbenoids

| Concentration (μg/ml) | Sirtinol 2-[(2-Hydroxynaphthalen-1-ylmethylene)amino]-N-(1-phenyl-ethyl)•benzamide | Resveratrol | Pterostilbene | Gnetol | 3-hydroxyPterostilbene (3hp) | Oxyresveratrol |
|---|---|---|---|---|---|---|
| 1 | 64.44 | 137.78 | 2.22 | 104.44 | 224.44 | 77.78 |
| 10 | −23326.67 | 291.11 | 11.11 | 1846.67 | 668.89 | 24.44 |
| 50 | −57517.78 | 1137.78 | 53.33 | 3686.67 | 1946.67 | 60.00 |
| 100 | −60093.33 | 1471.11 | 113.33 | 4151.11 | 3146.67 | 202.22 |
| 250 | −56544.44 | 1902.22 | 231.11 | 4826.67 | 3771.11 | 297.78 |

EXAMPLE II

Tables B, C, D and E

Antimicrbial Studies of 3-Hydroxy Pterostilbene Against *Propionibacterium Acnes*

Objective:

To compare the effect of 3-Hydroxypsterostilbene and Resveratrol on *Propionibacterium acnes* growth.

*Propionibacterium acnes* is a gram-positive, non-spore forming, anaerobic, pleomorphic rod found in clinical specimens. In human body *P. acnes* thrives on areas most exposed to air, such as the face and the nose. Its ability to live as an anaerobic in an air-exposed environment comes from the fact that *P. acnes* lives in the microhabitat sebaceous follicles thus causing acne vulgaris.

Method:

Disc diffusion method was done to study Minimum inhibitory concentration (MIC).

Materials

1. *Propionibacterium* acnes ATCC 11827
2. Physiological saline or Buffered peptone water (BPW).
3. Reinforced *clostridium* medium (RCM) Hi-media
4. Reinforced *clostridium* agar (RCA) Hi-media
5. Anaerobic chamber.
6. Gassing manifold Nitrogen, mixed gases.
7. Spectrophotometer (600 nm to 625 nm).
8. Sterile Petri plates (150 mm×90 mm).
9. Sterile micro pipettes and sterile micro tips.

TABLE B

| Sample: Resveratrol Batch: C81173 Concentration of sample % (w/v) | Zone of inhibition (mm) | Sample: 3-Hydroxy Pterostilbene Batch: P80096 Concentration of sample % (w/v) | Zone of inhibition (mm) |
|---|---|---|---|
| 5.0 | 13.0 | 5.0 | 18.0 |
| 2.5 | 13.0 | 2.5 | 17.0 |
| 1.25 | 12.0 | 1.25 | 15.0 |
| 0.625 | 10.0 | 0.625 | 13.0 |
| 0.31 | No zone | 0.31 | 10.0 |
| 0.156 | No zone | 0.156 | No zone |

TABLE B-continued

| Sample: Resveratrol Batch: C81173 Concentration of sample % (w/v) | Zone of inhibition (mm) | Sample: 3-Hydroxy Pterostilbene Batch: P80096 Concentration of sample % (w/v) | Zone of inhibition (mm) |
|---|---|---|---|
| 0.078 | No zone | 0.078 | No zone |
| DMSO | No zone | DMSO | No zone |

Clindac A® (Galderma India Pvt. Ltd., Mumbai) anti-acne gel was used as Reference standard (Table C)

TABLE C

| Clindamycin phosphate USP (Anti acne cream) | Concentration (% w/v) | Zone of inhibition (mm) |
|---|---|---|
| SL. No. | | |
| 01 | 1 | 8.0 |
| 02 | 0.1 | No-zone |
| 03 | 0.05 | No-zone |
| Sterile water | As such | No-zone |

Sample Preparation: Sterilized DM Water

Discussion and Inference

From the studies 3-Hydroxy pterostilbene at 3.12 mg/ml (0.312% w/v) concentration produced a zone of inhibition of 10 mm while a higher concentration of resveratrol 6.25 mg/ml (0.625% w/v) was required to produce a similar effect. Reference standard Clindac A® produced a 8 mm zone of inhibition at a concentration of 10 mg/ml (1.0% w/v).

Inhibitory Concentration ($IC_{50}$ and $IC_{100}$) Evaluation Studies

Method:

Broth dilution method to evaluate the inhibitory concentration (IC).

Materials

1. *Propionibacterium acnes* ATCC: 11827
2. Physiological saline or Buffered peptone water (BPW).
3. Reinforced *clostridium* medium (RCM) Hi-media
4. Actinomyces broth (AC broth) Hi-media
5. Anaerobic chamber.
6. Gassing manifold Nitrogen, mixed gases.
7. Spectrophotometer (600 nm to 625 nm).
8. Sterile tubes
9. Micro Pipette
10. Sterile micro tips.
11. (DMSO) dimethylsulphoxide The strain *Propionibacterium acnes* (ATCC 11827) was obtained from ATCC. The inhibitory concentration (IC) of the given sample was determined by broth dilution method according to NCCLS guidelines. The $IC_{50}$ was defined as that concentration of compound that reduced bacterial growth by 50% as determined spectrophotometrically. $IC_{100}$ was defined as the lowest concentration of compound that inhibited bacterial growth by 100% Resveratrol and 3-Hydroxypsterostilbene are water insoluble. Therefore samples were dissolved in DMSO and than added to Actinomyces broth to a final concentration of 0-500 mg/L. Twenty-four hour cultures of *P. acnes* were adjusted to $1 \times 10^8$ cfu/ml using McFarland standards and inoculated to Actinomycetes broth containing a specific concentration of compound. Controls containing just DMSO were also included in the test. Cultures were incubated anaerobically at 37° C. and read spectrophotometrically at 600 nm both at 24 h and 48 h incubation periods. $IC_{50}$ and $IC_{100}$ values were calculated from these observations.

TABLE D

| | | | | Results | | |
|---|---|---|---|---|---|---|
| Sample | Conc. (mg/L) | Dilution | OD @ 600 nm 24 h | (IC) Inhibitory concentration | OD @ 600 nm 48 h | (IC) Inhibitory concentration |
| AC broth | NA | As such | 0.131 | NA | 0.126 | NA |
| AC broth + culture | NA | 1:2 | 0.942 | NA | 0.820 | NA |
| 3-Hydroxy psterostilbene | 16.6 | 1:2 | 0.526 | IC 45 | 0.443 | IC 45 |
| | 41.6 | 1:2 | 0.352 | IC 62 | 0.338 | IC 62 |
| | 83.3 | As such | 0.047 | IC 98 | 0.073 | IC 98 |
| | 166 | As such | — | IC 100 | — | IC 100 |
| | 332 | As such | — | IC 100 | — | IC 100 |
| Resveratrol | 16.6 | 1:2 | 1.027 | No inhibition | 0.884 | No inhibition |
| | 41.6 | 1:2 | 0.777 | IC 17 | 0.593 | IC 27 |
| | 83.3 | 1:2 | 0.423 | IC 55 | 0.573 | IC 30 |
| | 166 | 1:2 | 0.232 | IC 75 | 0.268 | IC 68 |
| | 332 | As such | 0.00 | IC 100 | 0.11 | IC 85 |
| | 498 | As such | — | IC 100 | 0.00 | IC 100 |

NA: Not applicable

Discussion and Inference (Table E)

TABLE E

| SAMPLE | STRAIN | IC50 (mg/L) 24 h | IC100 (mg/L) 24 h | IC50 (mg/L) 48 h | IC100 (mg/L) 48 h |
|---|---|---|---|---|---|
| 3-Hydroxy pterostilbene P80096 | *P. acnes* ATCC 11827 | 33.5 | 83.3 | 35.8 | 83.0 |
| Resveratrol C81173 | *P. acnes* ATCC 11827 | 83.0 | 332.0 | 120 | 498 |
| DMSO | *P. acnes* ATCC 11827 | No inhibition | No inhibition | No inhibition | No inhibition |

Conclusion

From the inhibitory concentration studies, both Resveratrol and 3-HydroxyperoStilbene were capable of inhibiting *P. acnes* growth. 3-Hydroxypero-stilbene was found to be more effective against *P. acnes*. 3-hydroxypterostilbene showed 100% inhibition of *Propionibacterium acnes* at concentrations of 83.3 mg/ml and 83 mg/ml following 24 hours and 48 hours of incubation respectively. While resveratrol showed 100% inhibition of *Propionibacterium acnes* at concentrations of 332 mg/ml and 498 mg/ml following 24 hours and 48 hours of incubation respectively.

EXAMPLE III

Pharmacokinetic Studies

Figure 2A:
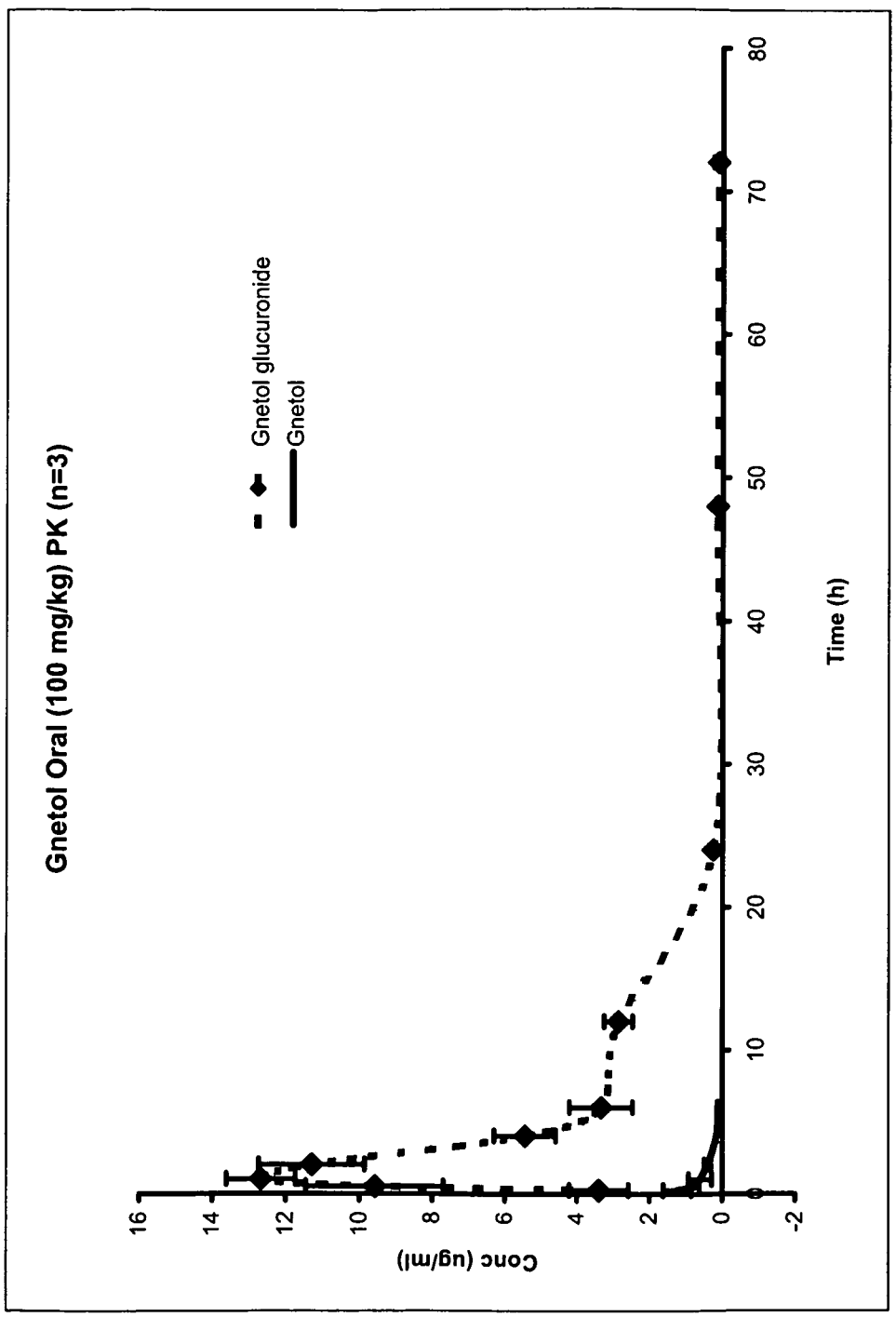
FIGS. 2A and 2B show the graphical representations of 2,3',5',6-tetrahydroxy-trans-stilbene (gnetol) pharmacokinetics in the serum upon oral administration in animals.
Figure 2B:
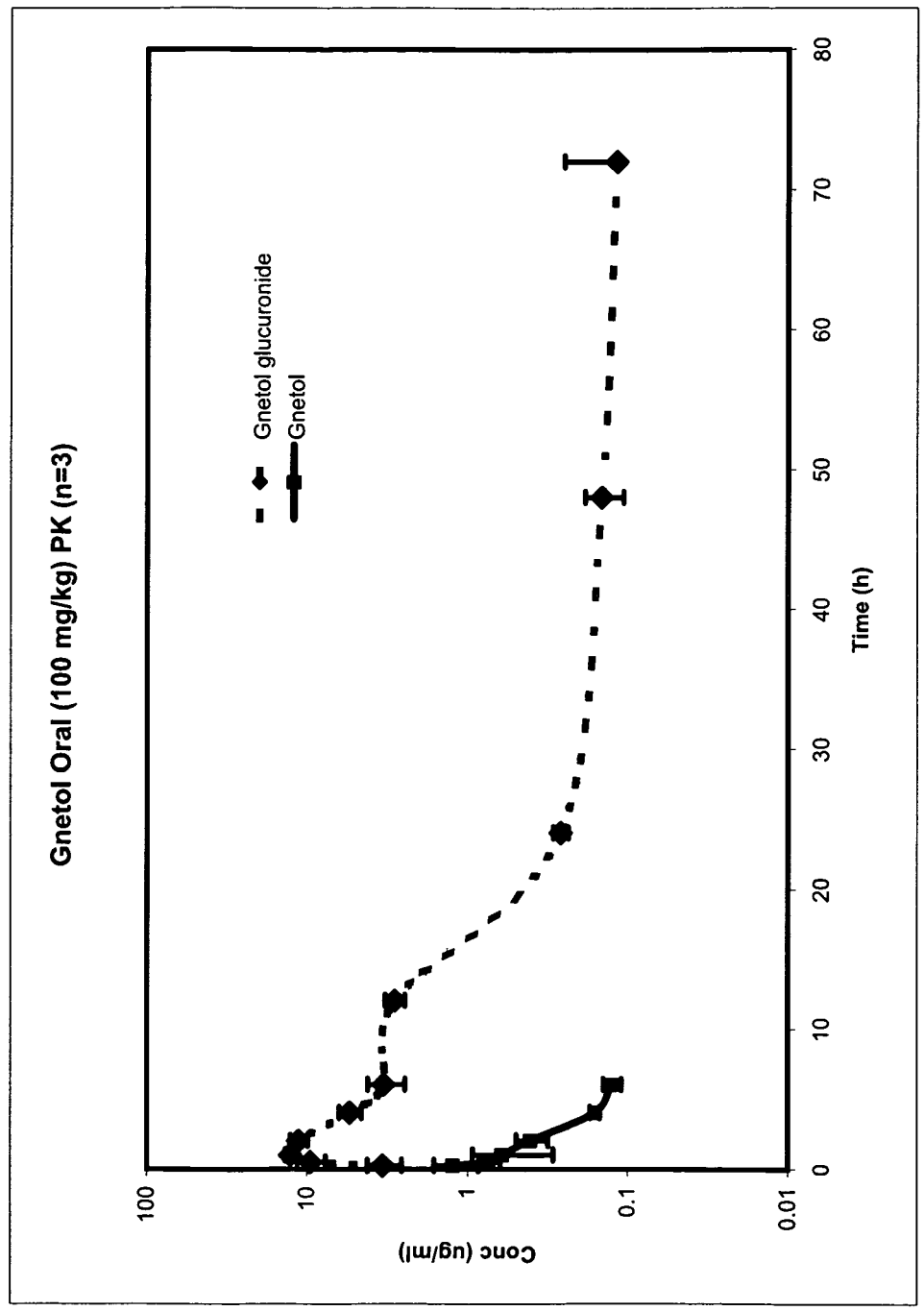
Figure 3A:
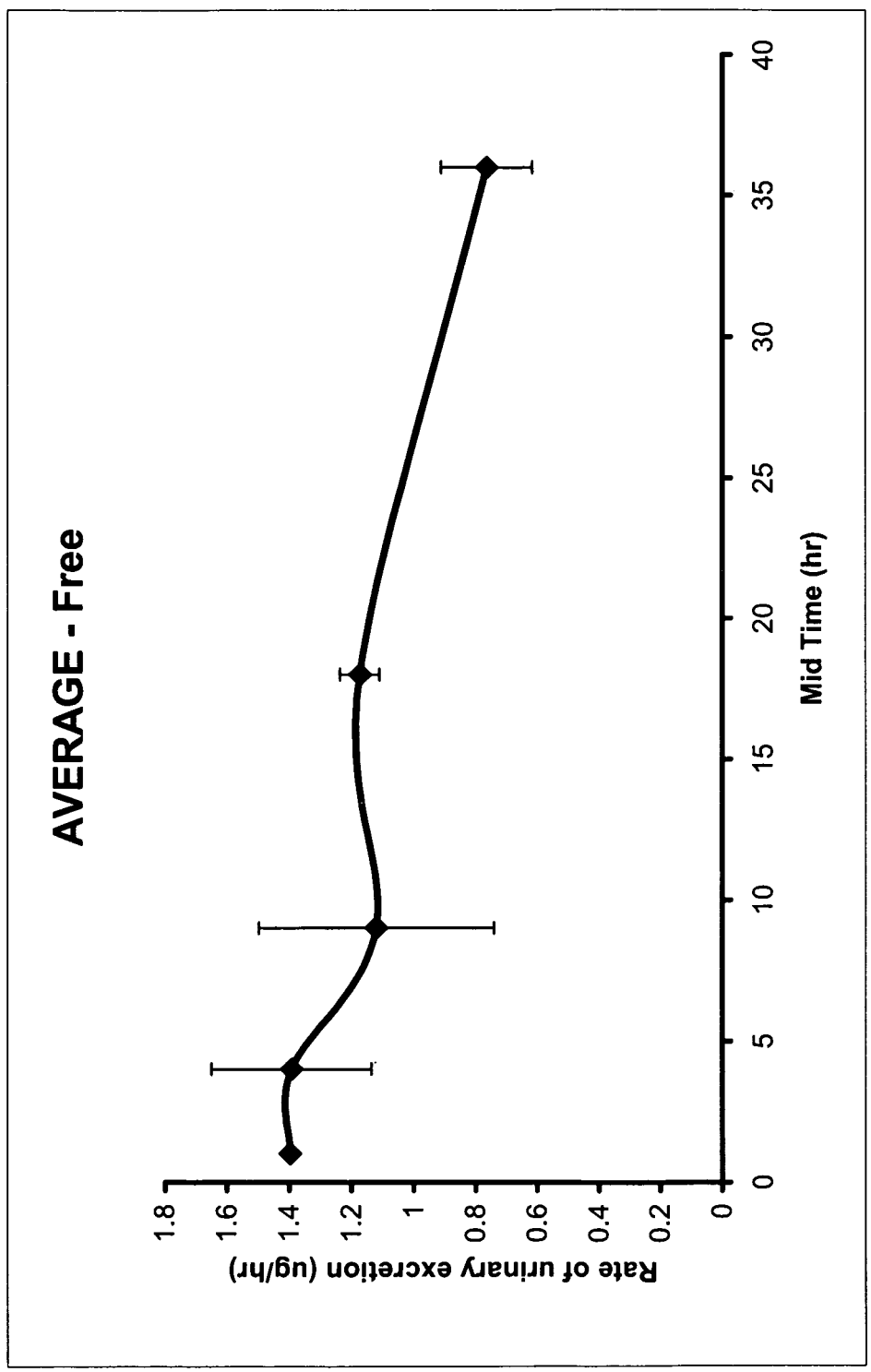
FIGS. 3A, 3B and 3C shows the graphical representations of 2,3',5',6-tetrahydroxy-trans-stilbene (gnetol) pharmacokinetics in the urine upon oral administration in animals.
Figure 3B:
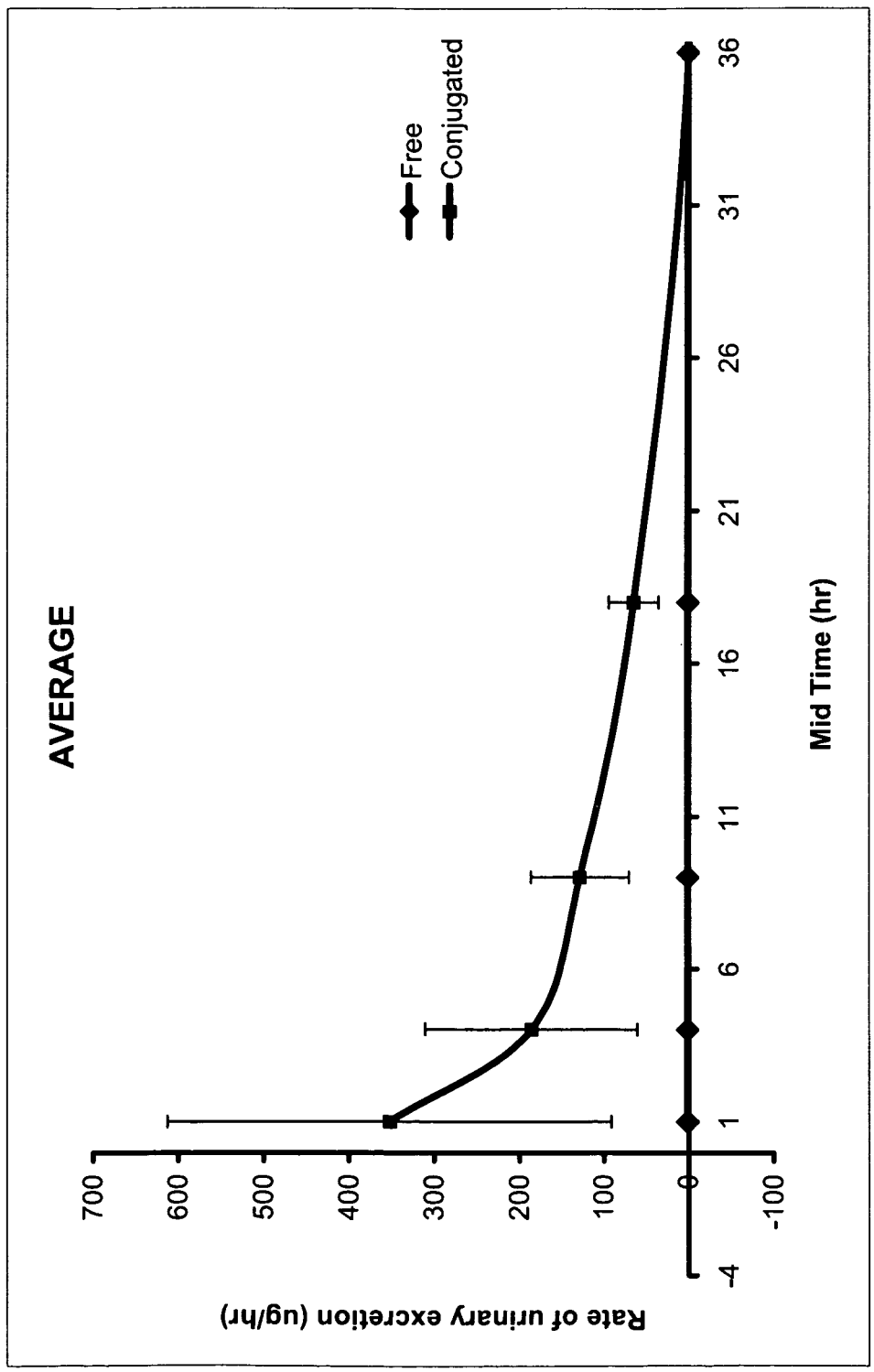
Figure 3C:
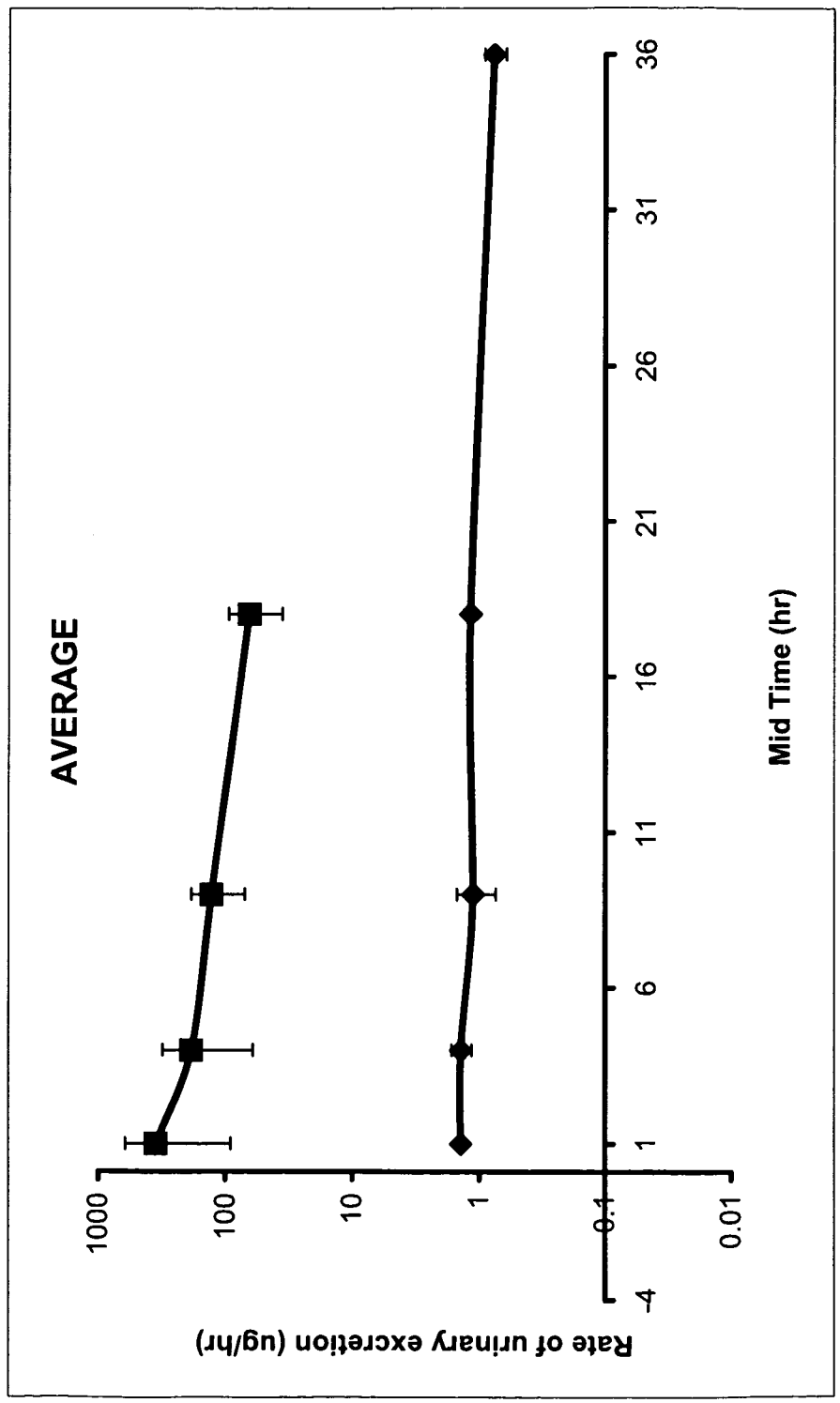

FIGS. 2A and 2B reveal that upon oral administration in rats of 100 mg/kg body weight, it is evident that 2,3',5',6-tetrahydroxy-trans-stilbene (gnetol) in its free form and as a glucoronide is orally bioavailable. The compound in its free and conjugated form is freely absorbed into systemic circulation with the glucoronide detected up to 72 hours. FIGS. 3A, 3B and 3C reveal that 2,3',5',6-tetrahydroxy-trans-stilbene (gnetol) is excreted predominantly as glucoronides in the urine, with glucoronides exhibiting a better rate of excretion.

Figure 4:
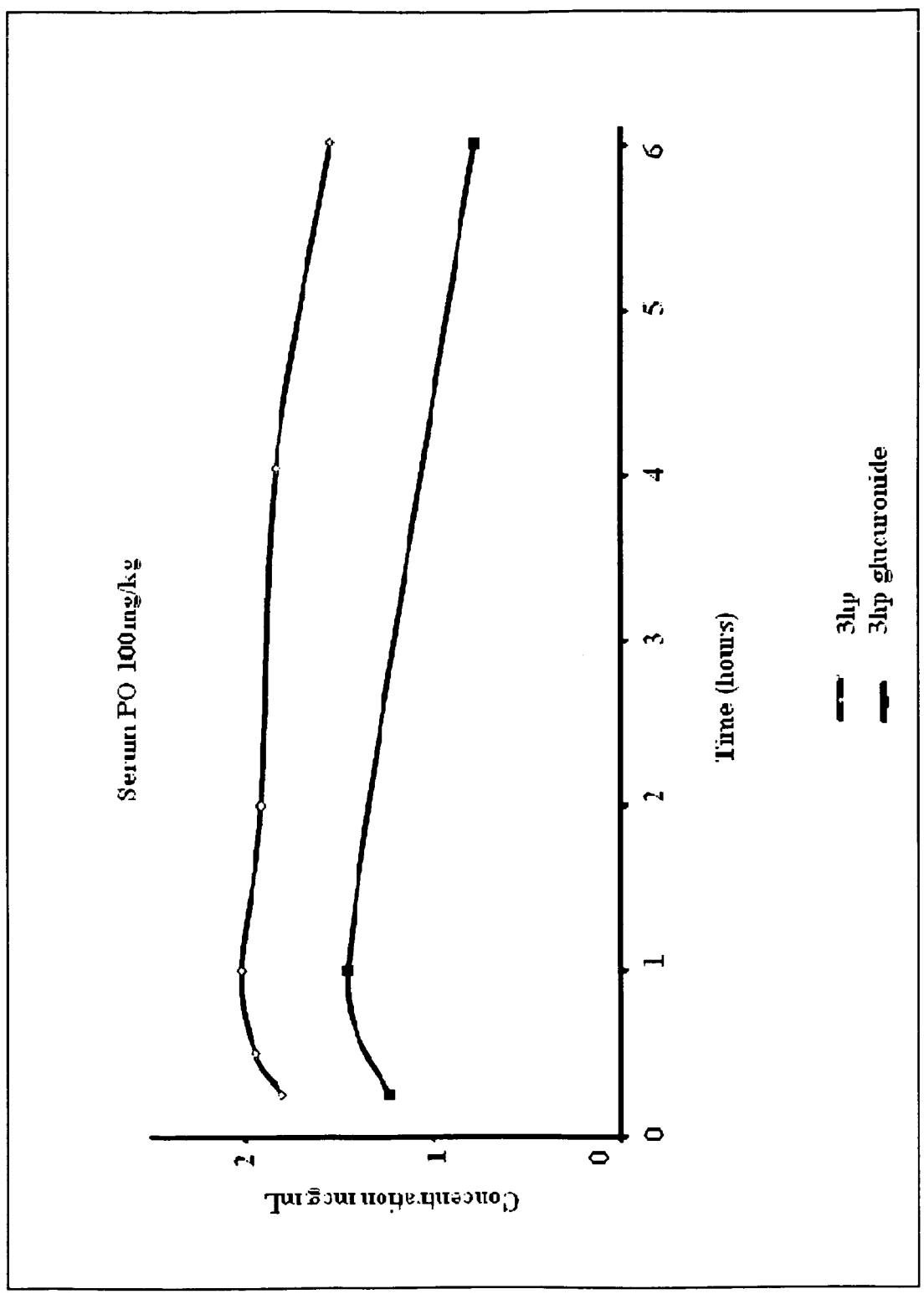
FIG. 4 shows the graphical representations of 3,5-dimethoxy-3,4'-dihydroxystilbene pharmacokinetics in the serum upon oral administration in animals.
Figure 5A:
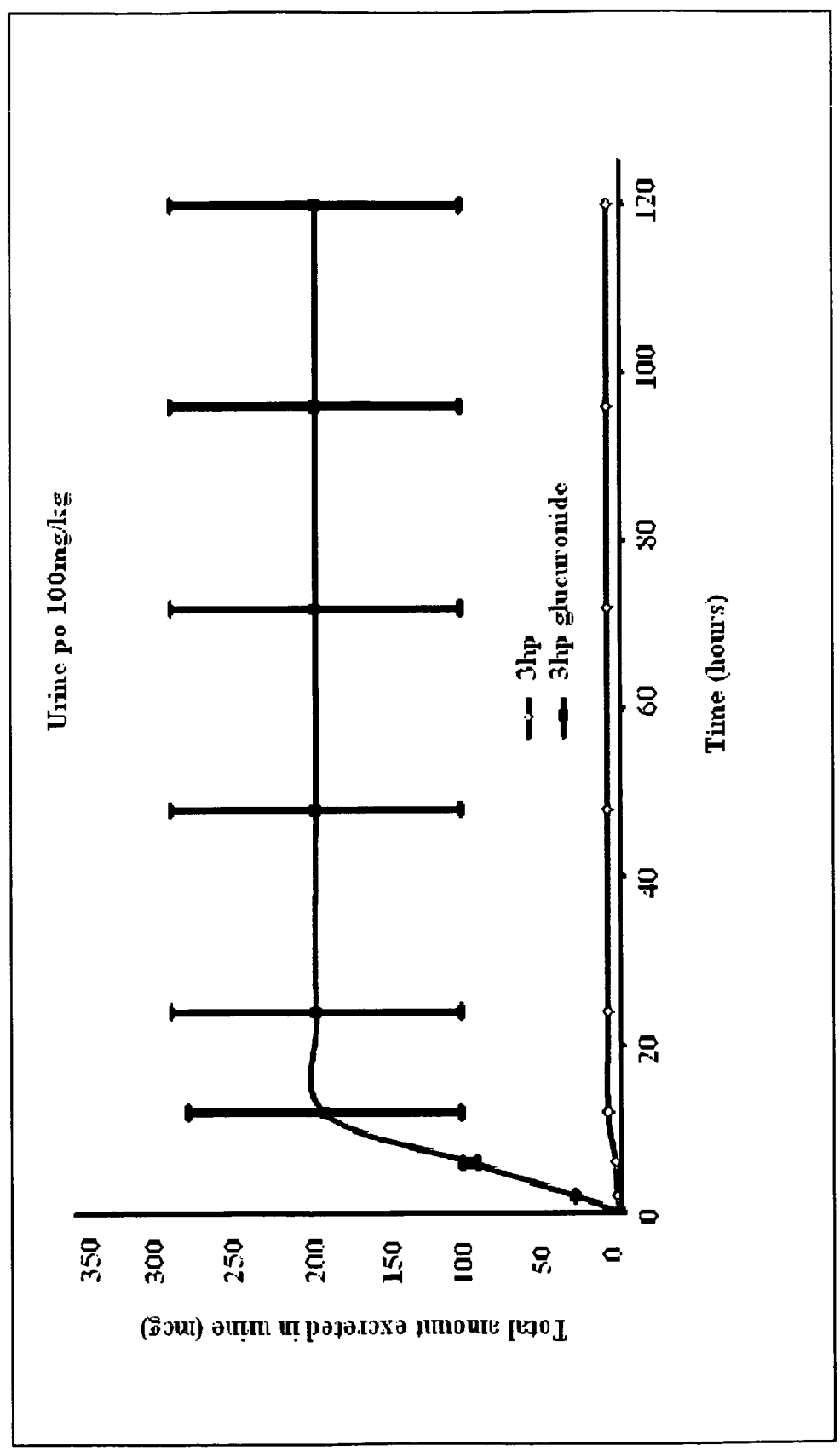
FIGS. 5A and 5B shows the graphical representations of 3,5-dimethoxy-3,4'-dihydroxystilbene pharmacokinetics in the urine upon oral administration in animals.
Figure 5B:
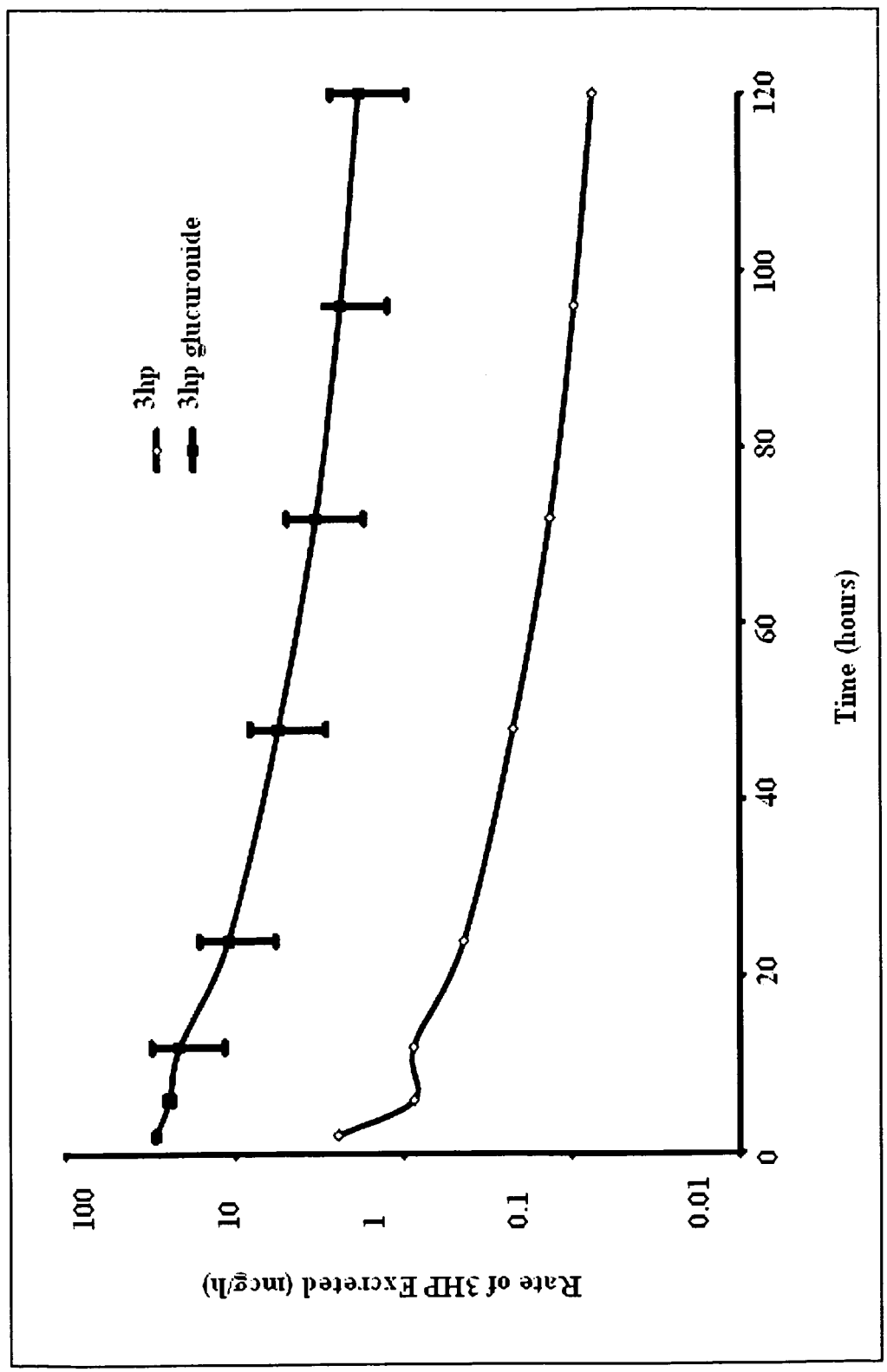

Upon oral administration in rats of 100 mg/kg body weight, it is evident that 3,5-dimethoxy-3,4'-dihydroxystilbene (3-hydroxypterostilbene) in its free form and as a glucoronide is orally bioavailable. (FIG. 4). The compound in its free and conjugated form appears in systemic circulation within 15 minutes of administration. 3,5-dimethoxy-3,4'-dihydroxystilbene (3-hydroxypterostilbene) is excreted predominantly as glucoronides in the urine, with glucoronides exhibiting a better rate of excretion (FIGS. 5A and 5B).

REFERENCES

1. John J. Docherty, Heather A. McEwen, Thomas J. Sweet, Erin Bailey and Tristan D. Booth: "Resveratrol inhibition of *Propionibacterium acnes*"; Journal of antimicrobial chemotherapy (2007) 59, 1182-1184. Advance Access publication 21 Apr. 2007;
2. National committee for clinical laboratory standards—Methods for Antimicrobial susceptibility testing of Anaerobic Bacteria—fifth edition: Approved standards M11-A6.NCCLS, Wayne, Pa., USA, 2000

EXAMPLE III

Cosmeceutical formulations comprising 3,5-dimethoxy-3,4'-dihydroxystilbene (3-hydroxypterostilbene)

Cosmeceutical Formulation I

| S. No. | Formula | Content % w/w |
|---|---|---|
| 1 | 3,5-dimethoxy-3,4'-dihydroxystilbene | 0.25-5 |
| 2 | Tetra sodium EDTA | 0.02 |
| 3 | Imidurea | 0.15 |
| 4 | Sodium Methyl paraben | 0.20 |
| 5 | Sodium Propyl paraben | 0.02 |
| 6 | Propylene glycol | 2.00 |
| 7 | Carbopol U-10 | 0.20 |
| 8 | Pemulene TR-1 | 0.15 |
| 9 | GMS SE | 1.00 |
| 10 | Arlatone 2121 | 1.00 |
| 11 | Arlacel 165 | 1.00 |
| 12 | Elsoft | 2.00 |
| 13 | Elcast H | 2.00 |
| 14 | Sodium Hydroxide (20% NaOH solution) | 0.10 |
| 15 | DC 3031 Fluid | 0.50 |
| 16 | Demineralised water | 84.66-89.41 |
|  |  | 100.00 |

Cosmeceutical Formulation II

| S. No. | Formula | Content % w/w |
|---|---|---|
| 1 | 3,5-dimethoxy-3,4'-dihydroxystilbene | 0.25-5 |
| 2 | Tetra sodium EDTA | 0.02 |
| 3 | Imidurea | 0.15 |
| 4 | Sodium Methyl paraben | 0.20 |
| 5 | Sodium Propyl paraben | 0.02 |
| 6 | Propylene glycol | 2.00 |
| 7 | Carbopol U-10 | 0.30 |
| 8 | Pemulene TR-1 | 0.20 |
| 9 | GMS SE | 1.00 |
| 10 | Arlatone 2121 | 1.00 |
| 11 | Arlacel 165 | 1.00 |
| 12 | Fluilan (Liquid lanolin) | 2.00 |
| 13 | CCTG | 2.00 |
| 14 | Kokum butter | 0.50 |
| 15 | Sodium Hydroxide (20% NaOH solution) | 0.10 |
| 16 | DC 3031 Fluid | 0.50 |
| 17 | Demineralised water | 84.01-88.76 |
|  |  | 100.00 |

Cosmeceutical Formulation III

| S. No. | Formula | Content % w/w |
|---|---|---|
| 1 | 3,5-dimethoxy-3,4'-dihydroxystilbene | 0.25-5 |
| 2 | Carbopol U-10 | 0.20 |
| 3 | Pemulene TR-1 | 0.15 |
| 4 | Glycerine | 2.00 |
| 5 | Arlatone 2121 | 1.00 |
| 6 | GMS SE | 2.00 |
| 7 | Crill 4 | 2.00 |
| 8 | Jojoba oil | 2.00 |
| 9 | Kokum butter | 0.50 |
| 10 | Triethanolamine | 1.00 |
| 11 | Neolon PE | 0.50 |
| 12 | Demineralised water | 84.70-87.45 |
|  |  | 100.00 |

Cosmeceutical Formulation IV (Lotion)

| S. No. | Formula | Content % w/w |
|---|---|---|
| 1 | 3,5-dimethoxy-3,4'-dihydroxystilbene | 0.25-5 |
| 2 | Tetra sodium EDTA | 0.05 |
| 3 | Imidurea | 0.50 |
| 4 | Methyl paraben | 0.25 |
| 5 | Propyl paraben | 0.10 |
| 6 | Propylene glycol | 3.00 |
| 7 | Glycerine | 3.00 |
| 8 | GMS SE | 1.00 |
| 9 | CCTG | 1.00 |
| 10 | Iso Propyl Myristate | 2.00 |
| 11 | Light liquid Prarffin | 1.75 |
| 12 | Soft Paraffin | 1.00 |
| 13 | Polawax | 1.00 |
| 14 | DC 3031 Fluid | 0.30 |
| 15 | Salcare SC-91 | 0.60 |
| 16 | Demineralised water | 79.45-84.20 |
|  |  | 100.00 |

Nutraceutical/Pharmaceutical Formulations 3-hydroxypterostilbene Tablet

Label Claim: Each tablet contains: 3-hydroxypterostilbene=250 mg

Composition

| | |
|---|---|
| 1. 3-hydroxypterostilbene = | 250 mg |
| 2. Microcrystalline cellulose BP = | 190.0 mg |
| 3. Maize Starch BP = | 40.0 mg |
| 4. Magnesium Stearate BP = | 5.0 mg |
| 5. Sodium Starch Glycolate BP = | 15.0 mg |

3-hydroxypterostilbene Capsules

Label Claim: Each Capsule contains 3-hydroxypterostilbene=250 mg

Composition

| | |
|---|---|
| 1. 3-hydroxypterostilbene = | 250 mg |
| 2. Microcrystalline cellulose BP = | 38.0 mg |
| 3. Maize Starch BP = | 10.0 mg |
| 4. Magnesium Stearate BP = | 2.0 mg |
| 5. Hard Gelatin Capsules Size '1' | |

Gnetol Capsules

Label Claim: Each Capsule contains: Gnetol=250 mg

Composition

| | |
|---|---|
| 1. Gnetol = | 250 mg |
| 2. Microcrystalline cellulose BP = | 38.0 mg |
| 3. Povidone BP = | 10.0 mg |
| 4. Magnesium Stearate BP = | 2.0 mg |
| 5. Hard Gelatin Capsules Size '1' | |

Gnetol Tablets

Label Claim: Each tablet contains Gnetol=250 mg

Composition

| | |
|---|---|
| 1. Gnetol = | 250 mg |
| 2. Microcrystalline cellulose BP = | 190.0 mg |
| 3. Povidone BP = | 40.0 mg |
| 4. Magnesium Stearate BP = | 5.0 mg |
| 5. Sodium Starch Glycolate BP = | 15.0 mg |

3-hydroxypterostilbene and Gnetol Tablets

Label Claim:

Each tablet contains 3-hydroxypterostilbene=100 mg AND Gnetol=100 mg

Composition

| | |
|---|---|
| 1. 3-hydroxypterostilbene = | 100 mg |
| 2. Gnetol = | 100 mg |
| 3. Microcrystalline cellulose BP = | 240.0 mg |
| 4. Maize Starch BP = | 40.0 mg |
| 5. Magnesium Stearate BP = | 5.0 mg |
| 6. Sodium Starch Glycolate BP = | 15.0 mg |

3-hydroxypterostilbene and Epicatechin Capsules

Label Claim: Each tablet contains 3-hydroxypterostilbene=250 mg and Epicatechin=250 mg Composition

| | |
|---|---|
| 1. 3-hydroxypterostilbene = | 250 mg |
| 2. Epicatechin = | 25.0 mg |
| 3. Microcrystalline cellulose BP = | 13.0 mg |
| 4. Maize Starch BP = | 10.0 mg |
| 5. Magnesium Stearate BP = | 2.0 mg |
| 6. Hard Gelatin Capsules Size '1' | |

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of enhanced modulation of human sirtuin I, said method comprising step of bringing into contact human sirtuin I with the compound of STR#1 composition containing a compound of STR#1 to achieve the effect of human sirtuin activation

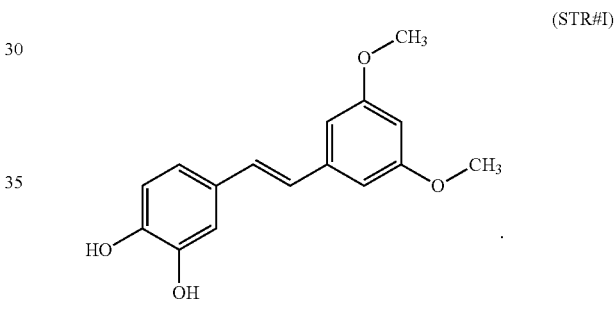

(STR#I)

2. A method of enhanced modulation of human sirtuin I activity using compound of STR#2 or composition containing a compound of STR#2, said method comprising step of bringing into contact human sirtuin I with the compound of STR#2 or composition containing a compound of STR#2 to achieve the effect of human sirtuin I activation

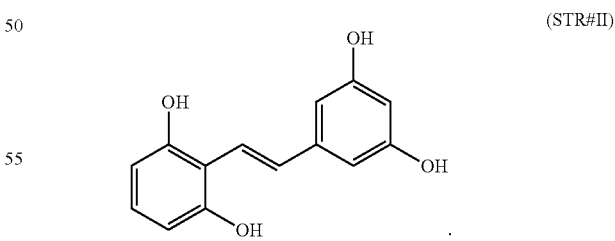

(STR#II)

* * * * *